United States Patent
Tanaka

(10) Patent No.: US 10,945,611 B2
(45) Date of Patent: Mar. 16, 2021

(54) EAR THERMOMETER

(71) Applicant: BIO ECHO NET INC, Sapporo (JP)

(72) Inventor: Hideki Tanaka, Sapporo (JP)

(73) Assignee: BIO ECHO NET INC., Sapporo (JP)

( * ) Notice: Subject to any disclaimer, the term of this patent is extended or adjusted under 35 U.S.C. 154(b) by 602 days.

(21) Appl. No.: 15/843,309

(22) Filed: Dec. 15, 2017

(65) Prior Publication Data

US 2018/0103850 A1    Apr. 19, 2018

Related U.S. Application Data

(63) Continuation of application No. PCT/JP2016/067105, filed on Jun. 8, 2016.

(30) Foreign Application Priority Data

Jun. 16, 2015   (JP) .............................. JP2015-120760

(51) Int. Cl.
| | |
|---|---|
| *G01J 5/00* | (2006.01) |
| *A61B 5/01* | (2006.01) |
| *A61B 5/00* | (2006.01) |
| *G01J 5/04* | (2006.01) |
| *G01K 13/00* | (2021.01) |

(52) U.S. Cl.
CPC .............. *A61B 5/01* (2013.01); *A61B 5/6817* (2013.01); *G01J 5/00* (2013.01); *G01J 5/049* (2013.01); *G01K 13/004* (2013.01); *A61B 5/0086* (2013.01)

(58) Field of Classification Search
CPC combination set(s) only.
See application file for complete search history.

(56) References Cited

U.S. PATENT DOCUMENTS

| | | |
|---|---|---|
| 3,581,570 A | 6/1971 | Wortz |
| 5,469,855 A | 11/1995 | Pompei et al. |
| 6,011,891 A | 1/2000 | Katzir et al. |

(Continued)

FOREIGN PATENT DOCUMENTS

| | | |
|---|---|---|
| CN | 100535619 A | 4/2007 |
| CN | 202889572 U | 4/2013 |
| JP | 6319705 A | 11/1994 |

(Continued)

OTHER PUBLICATIONS

Decision to Grant for related Taiwanese application No. TW105118784 dated May 5, 2017.

(Continued)

*Primary Examiner* — Lisa M Caputo
*Assistant Examiner* — Nasir U. Ahmed
(74) *Attorney, Agent, or Firm* — Procopio, Cory, Hargreaves & Savitch LLP

(57) ABSTRACT

A thermometer includes a probe to be fitted into an ear of a patient, the probe having an infrared sensor for measuring the temperature of an eardrum of the ear of the patient in a non-contact manner, a signal cable connected to the infrared sensor and drawn out of the probe, a gripping part provided in the probe to be gripped when the probe is inserted inside a tragus of the ear, and a groove portion provided in the gripping part to hold the signal cable in a curved state and to allow a curved portion of the signal cable to fit in and along a cavum conchae of the ear.

3 Claims, 7 Drawing Sheets

(56) References Cited

U.S. PATENT DOCUMENTS

2007/0091980 A1* 4/2007 Tanaka .................... G01J 5/16
374/121
2011/0110552 A1* 5/2011 Pang .................... H04R 1/1033
381/374

FOREIGN PATENT DOCUMENTS

| JP | 2010-145131 A | 7/2010 |
|----|---------------|--------|
| JP | 2013-13540 A | 1/2013 |
| TW | 201108990 A | 3/2011 |
| TW | 201210569 A | 3/2012 |
| WO | 2006091106 A1 | 8/2006 |

OTHER PUBLICATIONS

Decision to Grant for related Taiwanese application No. TW105118784 dated May 12, 2017. (Correcting the mail date).
Extended European Search Report for related EP App No. 16811523.6 dated Jan. 31, 2019, 6 pgs.
Office Action for related CN App No. 201680035305.3 dated Feb. 18, 2019, 5 pgs.

\* cited by examiner

EAR THERMOMETER

CROSS REFERENCE TO RELATED APPLICATIONS

This application is a continuation of International Application No. PCT/JP2016/067105, filed Jun. 8, 2016, and based upon and claims the benefit of priority from Japanese Patent Application No. 2015-120760, filed Jun. 16, 2015, the entire contents of all of which are incorporated herein by reference.

TECHNICAL FIELD

The present application relates to a continuous measuring and ear wearing type thermometer which is capable of continuously measuring a body temperature of a patient in a non-contact manner as a management index of the body temperature of the patient, for example, during an operation at an operation room, an intensive care unit (ICU), or the like.

BACKGROUND ART

At an operation room, an intensive care unit (ICU), or the like, it is essential to measure a body temperature of a patient during an operation. The measuring of the body temperature of the patient has to be continuously executed over a prolonged period of time. Also, the measuring of the body temperature of the patient has to be executed while reducing the burden on the patient.

As a conventional medical thermometer to meet such requirements, an ear thermometer which measures a temperature of an eardrum with a probe to be inserted into an ear hole of a patient is disclosed in JP 2010-145131 A.

SUMMARY

By the way, the ear thermometer of the conventional example has an infrared sensor arranged at a tip of the probe. The infrared sensor has to be fitted into to the ear hole so as to orientate toward the eardrum and thus obtain the quantity of infrared rays from the eardrum and its surrounding tissue for the purpose of acquiring a correct value of the body temperature.

In the ear thermometer of the conventional example, the shapes of the probe are individually provided for left and right so as to accord with the shapes of respective ear holes of the left and right ears of adult. This is because ear canals of the right and left ear holes of adult have individual bilateral symmetric curved shapes. In order that the shape of the probe corresponds to two different bilateral symmetrical curved shapes of the left and right ear holes of adult, probes of left and right thermometers have to be shaped like a mirror (with bilateral symmetric shapes).

Moreover, the probe of the thermometer of the conventional example is provided with an axis which allows a direction of the probe to be restricted when inserting the probe into the ear canal of the ear hole. Thus, if the probe is fitted so that this axis passes between a "tragus" and an "auricle", it means that the probe has been fitted in a correct position. In addition, with the probe constructed with such an axis as described above, it becomes possible to visually confirm that the probe has been fitted in the correct position.

On the other hand, the size of an ear hole of child is smaller than the size of an ear hole of adult and additionally, the curved shape of the ear canal of the ear hole of child is smaller than the curved shape of the ear canal of the ear hole of adult. For this reason, it is difficult to insert and fit the probe of the ear thermometer of the conventional example into the ear canal of the ear hole of child (for example, 4 to 12 years old).

Under the above situation, it is an object of the present application to provide a thermometer which can be easily and reliably fitted into an ear hole of child and by which the body temperature can be continuously measured in a stable state where the probe does not comes off the ear hole.

In order to achieve the above object, a thermometer according to an aspect of the present application includes: a probe to be fitted into an ear hole of a patient, the probe having an infrared sensor for measuring the temperature of an eardrum of an ear of the patient in a non-contact manner, a signal cable connected to the infrared sensor and drawn out of the probe, a gripping part provided in the probe to be gripped when the probe is inserted inside a tragus of the ear, and a groove portion provided in the gripping part to hold the signal cable in a curved state and to allow a curved portion of the signal cable to fit in and along a cavum conchae of the ear.

In the thermometer according to the aspect of the present application, an operator can fit the probe into an ear hole with the use of the gripping part. Moreover, since the signal cable is held by the groove portion of the gripping part, it is possible to allow the curved part of the signal cable to fit in and along the cavum conchae of the ear and also possible to retain the probe in the ear together with the signal cable. Therefore, the thermometer according to the aspect of the present application can be fitted into the ear hole of the ear of child both easily and reliably and can measure the body temperature continuously in a stable state where the thermometer does not come off the ear hole.

The groove portion may be configured so as to pinch and hold a portion of the signal cable.

With such a configuration, by only pinching and retaining the signal cable in the groove portion, it is possible to allow the signal cable in a curved state to fit in and along the cavum conchae of the ear both easily.

The gripping part may include a first projecting portion and a second projecting portion formed to face the first projecting portion, and the groove portion may be formed between the first projecting portion and the second projecting portion.

Thus, the groove portion of the gripping part is only defined by the first projecting portion and the second projecting portion. While having a simple structure, the first projecting portion and the second projecting portion hold the signal cable and moreover, the operator can grip the first projecting portion and the second projecting portion with fingers. The groove portion may be configured so as to bend a portion of the signal cable into a circular arc shape or a V shape.

By only forming the groove portion into a circular arc shape or a V shape, the first projecting portion and the second projecting portion hold the signal cable with a simple structure and moreover, the operator can grip the first projecting portion and the second projecting portion with fingers.

With the aspect of the present application, it is possible to provide a thermometer which can be easily and reliably fitted into an ear hole of child and by which the body temperature can be continuously measured in a stable state where the probe does not comes off the ear hole.

DESCRIPTION OF EMBODIMENTS

Thermometers according to embodiments will be described with reference to the drawings, below.

First Embodiment

A thermometer 1 according to a first embodiment will be described with reference to FIGS. 1 to 6.

Figure 1:
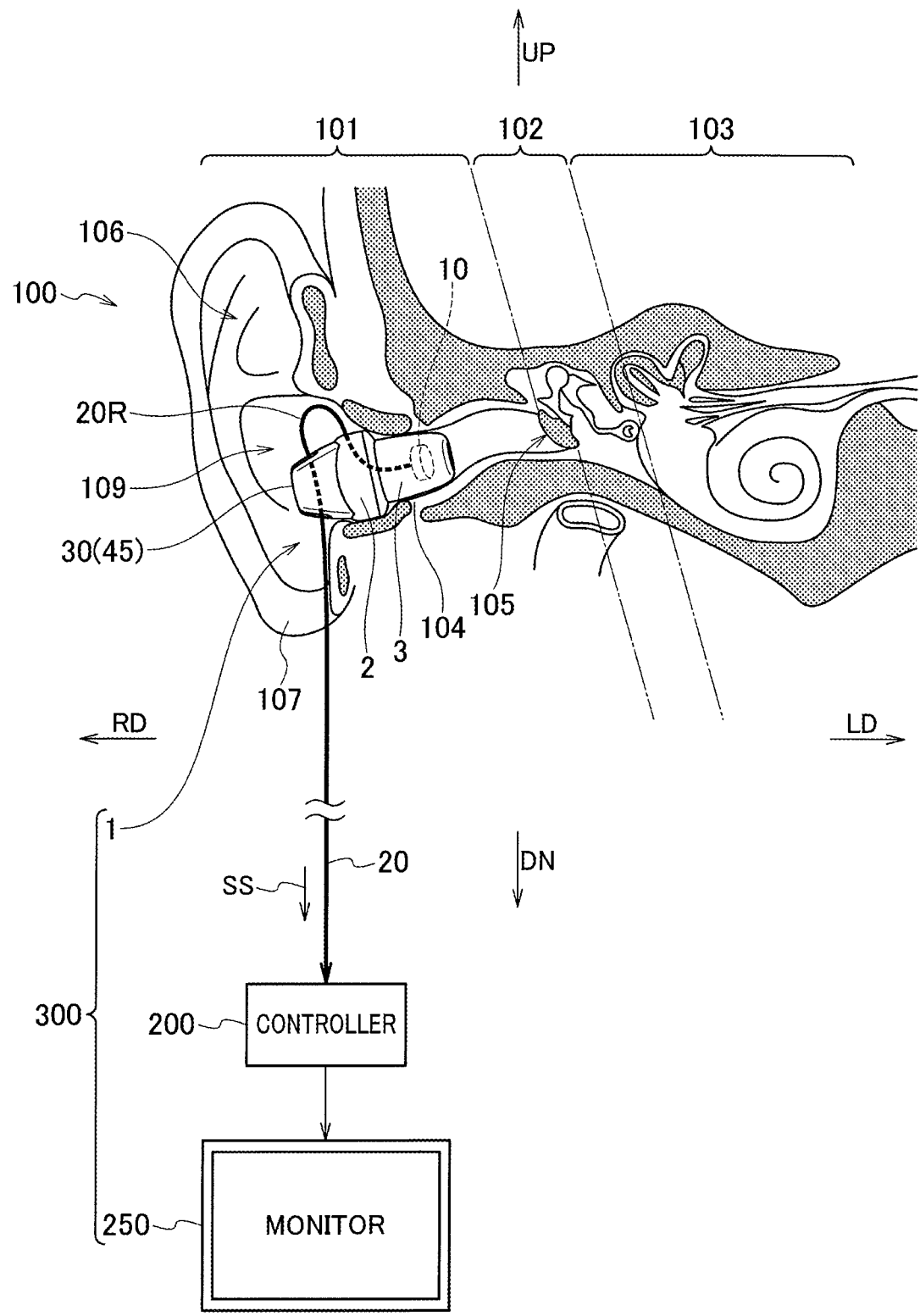
FIG. 1 is a view illustrating a state where a thermometer according to a first embodiment is fitted to an ear of patient.
Figure 2:
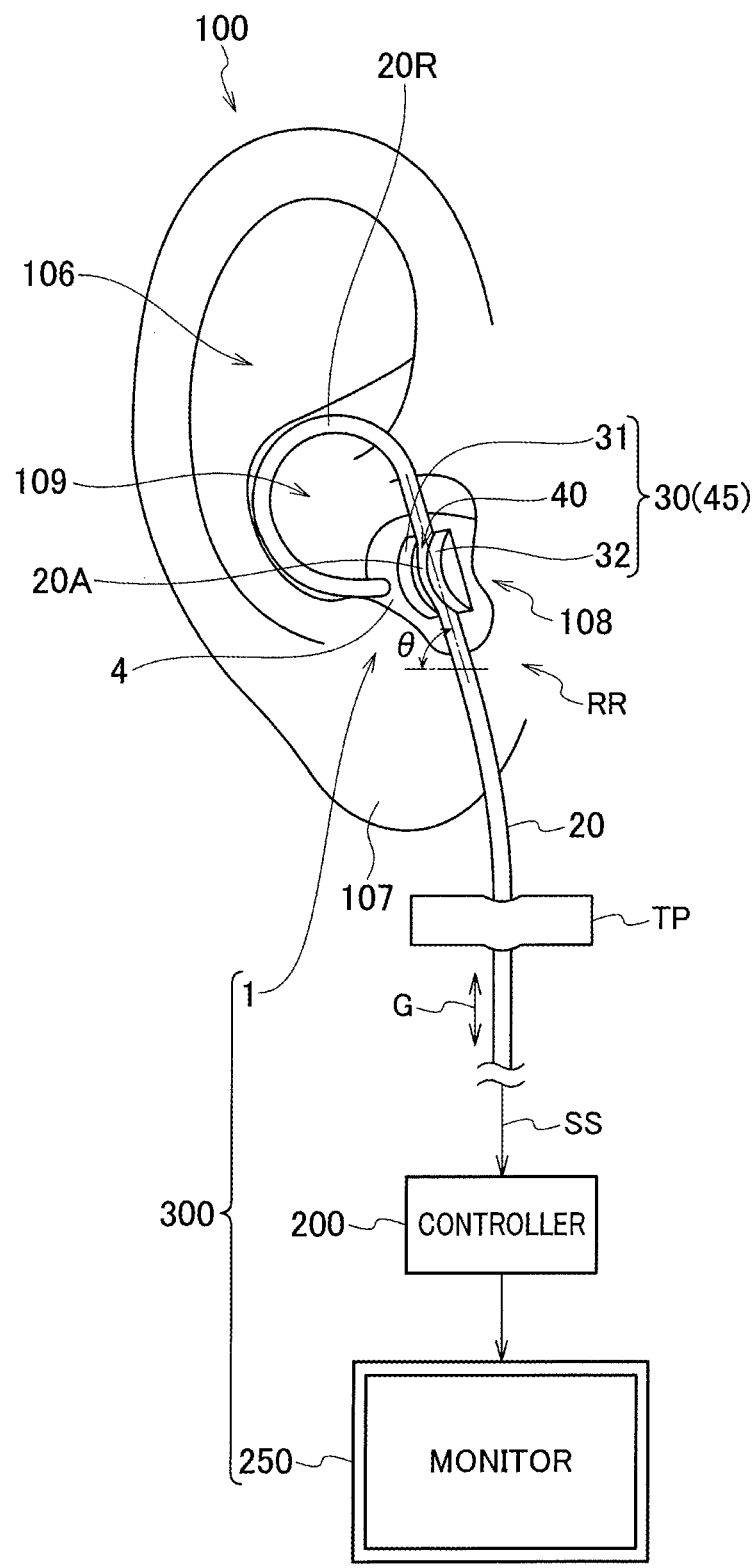
FIG. 2 is a side view illustrating the state where the thermometer according to the first embodiment is fitted to the ear of patient.

An ear 100 as illustrated in FIGS. 1 and 2 is a right ear of patient. In FIG. 1, an upward direction UP, a downward direction DN, a rightward direction RD, and a leftward direction LD of the human body are indicated using arrows. The left ear and the right ear have symmetrical structures.

The thermometer 1 according to the first embodiment is a continuous measuring and ear thermometer capable of continuously measuring the body temperature of patient in a non-contact manner. The thermometer 1 has an infrared sensor 10, and the thermometer 1 is fitted into an ear canal 104 as an ear hole of the ear 100. The infrared sensor 10 measures the amount of infrared rays from an eardrum 105 and its surrounding tissues inside the ear 100 of patient in a non-contact manner.

The thermometer 1 continuously measures the body temperature of patient in a non-contact manner as an index of temperature management of patient during an operation in an operation room, a physical condition management in an intensive care unit, or the like. The thermometer 1 is used to control the temperature of patient, preferably, child (for example, child from 4 to 12 years old). The thermometer 1 has a structure that allows it to be used in common for both the right ear 100 of patient and the left ear of patient having a symmetrical structure with the right ear 100.

Before explaining the structure of the thermometer 1, the structure of the ear 100 will be briefly described with reference to FIG. 1.

The ear 100 can be divided into an outer ear 101, a middle ear 102, and an inner ear 103. The outer ear 101 includes the ear canal 104 as an ear hole. There is the eardrum 105 at a boundary between the outer ear 101 and the middle ear 102. Additionally, the outer ear 101 includes an auricle 106, an earlobe 107, and a tragus 108. At the center of the auricle 106, there is a cavum conchae 109.

Next, a preferable structure example of the thermometer 1 will be described with reference to FIGS. 3 to 6.

Figure 3:
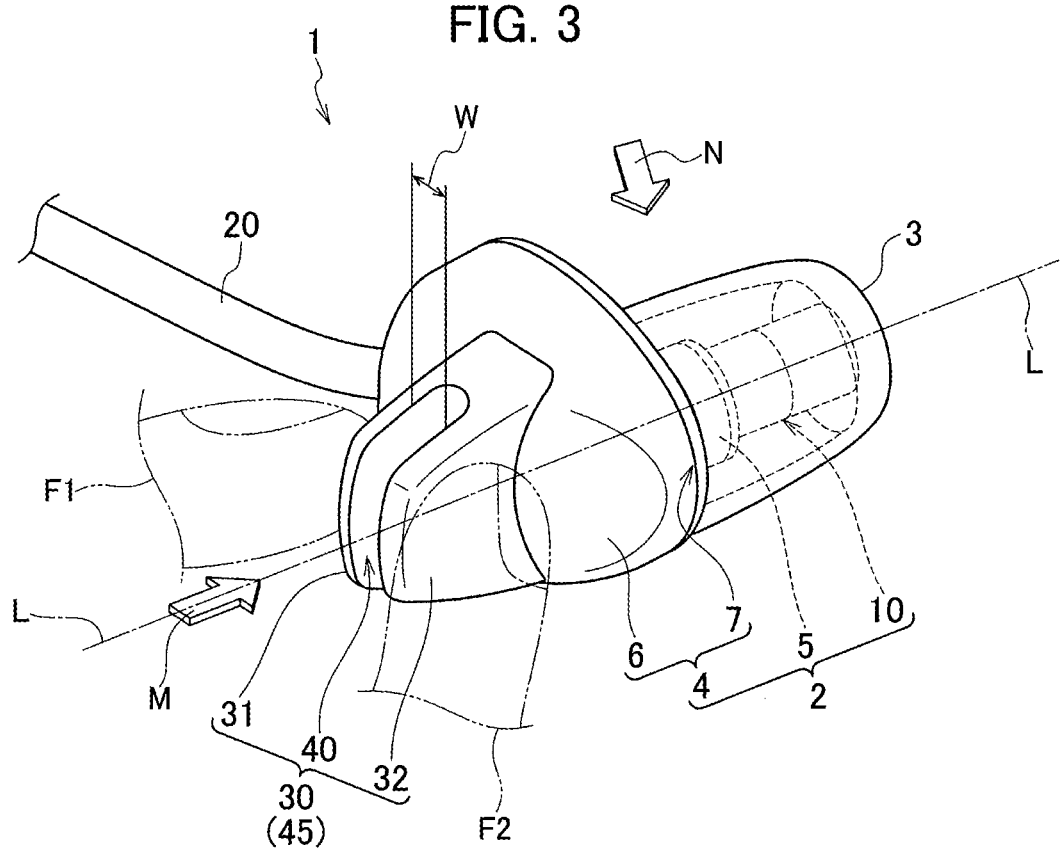
FIG. 3 is a perspective view illustrating the thermometer according to the first embodiment.
Figure 5:
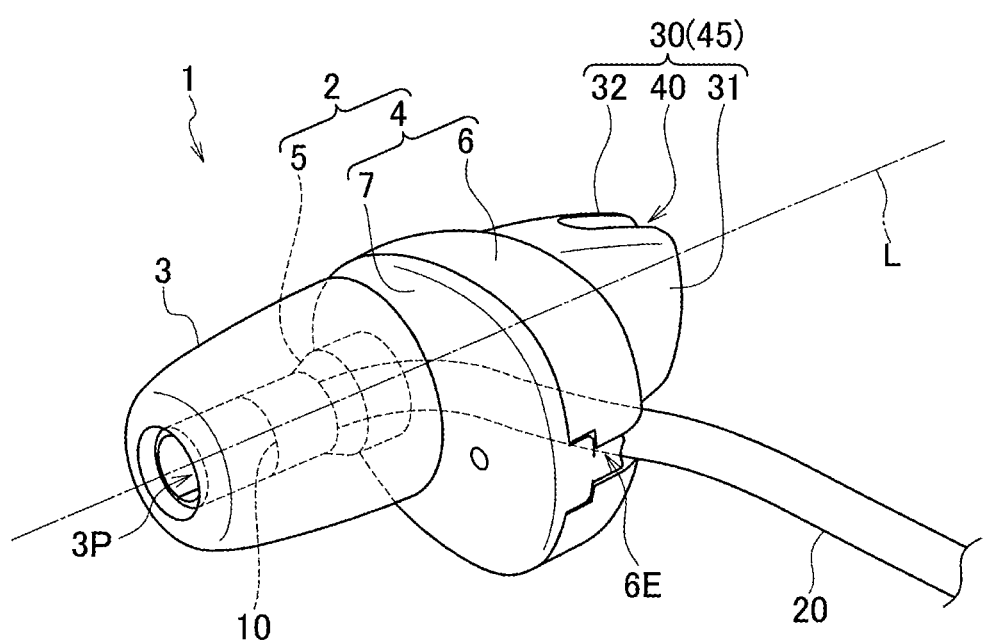
FIG. 5 is a perspective view of the thermometer according to the first embodiment, as viewed from an N direction of FIG. 3.

As illustrated in FIGS. 3 and 5, the thermometer 1 includes a probe 2, an ear pad 3, and a signal cable 20. The probe 2 includes a main body part 4, an inserting part 5 provided so as to project from the main body part 4, and the infrared sensor 10 attached to the inserting part 5. The ear pad 3 covers the inserting part 5 and the infrared sensor 10. The ear pad 3 is provided, at its tip part, with a circular opening 3P for transmitting infrared rays. The circular opening 3 P is positioned so as to correspond to the infrared sensor 10.

The infrared sensor 10 is electrically connected to one end part of a signal cable 20. As illustrated in FIG. 1, the other end part of the signal cable 20 is electrically connected to a controller (control unit) 200. The controller 200 is electrically connected to a monitor 250. The monitor 250 is a vital sign monitor. For example, a liquid crystal display device could be adopted as the monitor 250.

Consequently, the infrared rays radiated from the eardrum 105 and its surrounding tissues pass through the opening 3 P of the ear pad 3 of the probe 2 and reach the infrared sensor 10. Then, the infrared sensor 10 sends a detection signal SS corresponding to the amount of infrared rays radiated from the eardrum 105 and the surrounding tissues to the controller 200 via the signal cable 20.

Based on the detection signal SS corresponding to the amount of infrared rays incident on the infrared sensor 10, the controller 200 converts the detection signal SS into the temperature and establishes it as the body temperature value of patient. In accordance with a command from the controller 200, the monitor 250 displays the body temperature value of patient, preferably, together with various vital signs of patient.

The thermometer 1, the controller 200, and the monitor 250 constitute an ear temperature detection device 300. The ear temperature detection device 300 can be located in an operation room, an intensive care unit, or the like in order to continuously measure the body temperature in a non-contact manner at the time of the surgery in the operation room, the physical condition management in the intensive care unit, or the like.

Materials forming respective parts will be described below. Preferably, the probe 2 is made of plastics, for example, ABS resin (acrylonitrile butadiene styrene).

The ear pad 3 is a cylindrical probe cover that covers the inserting part 5 of the probe 2. The ear pad 3 is made of a soft material which is friendly for the ear 100, for example, silicone.

A coating material of the signal cable 20 is made of an ear-friendly and soft, such as PVC (polyvinyl chloride). As illustrated in FIGS. 1 and 2, the signal cable 20 is capable of forming a curved part 20R in a loop form inside the cavum conchae 109 without difficulty.

Next, the structure of the thermometer 1 will be described in detail, with reference to FIGS. 3 to 6.

The main body part 4 is provided by assembling a first member 6 and a second member 7 to each other. The first member 6 is swollen shaped and formed by a member that would be obtained by, for example, cutting the shell of an egg vertically in half.

Figure 4:
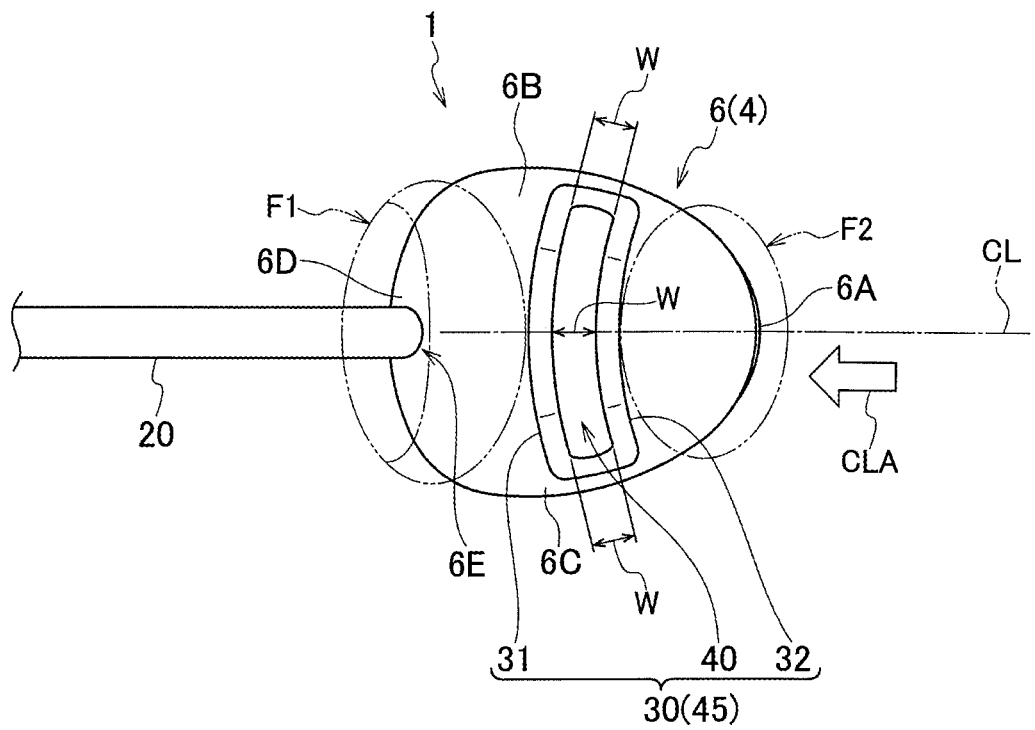
FIG. 4 is a side view of the thermometer according to the first embodiment, as viewed from an M direction of FIG. 3.

As illustrated in FIG. 4, the outer shape of the first member 6 includes a first arc portion 6A, two second arc portions 6B, 6C, and a third arc portion 6D. The second member 7 has an outer shape conforming to the first member 6 and includes a relatively flat member. The columnar inserting part 5 is formed so as to project from the second member 7.

The main body part 4 has a cable holding part 30 formed on its outer surface. The main body part 4 including the cable holding part 30 is bilateral symmetric with respect to a center line CL in the longitudinal direction so that the same part can be attached to either left or right ear of child.

As a result, the probe 2 can be fitted and mounted even in the left ear of child or even in the right ear 100 of child and therefore, the probe 2 has a shape allowing it to be worn on either of the right and left ears commonly.

As illustrated in FIG. 1, the probe 2 including the main body part 4 can be inserted and mounted in the vicinity of the entrance of the ear canal 104 of the ear 100. Further, as illustrated in FIG. 2, the probe 2 including the main body part 4 can be accommodated in the tragus 108. Nevertheless, as illustrated in FIG. 1, the cable holding part 30 projects from the ear canal 104 outward in a state where the probe 2 is attached to the ear 100.

As illustrated in FIG. 5, the third arc portion 6D has an opening 6E for leading the signal cable 20 out of the main body part 4. The signal cable 20 with its one end part connected to the infrared sensor 10 passes through the interior side of the main body part 4 and is led out of the main body part 4 through the opening 6E.

The main body part 4 includes the cable holding part 30. The cable holding part 30 is arranged so as to project from the first member 6. As illustrated in FIG. 3, assuming that the axis passing through the main body part 4 of the probe 2 and the inserting part 5 is a center axis L, the cable holding part 30 is arranged so as to project in the opposite direction to the inserting part 5 along the center axis L. The center axis L intersects with a center line CL in the longitudinal direction.

As illustrated in FIG. 2, the cable holding part 30 includes a groove portion 40 for interposing and holding a portion 20A of the signal cable 20. The cable holding part 30 includes a first projecting portion 31 and a second projecting portion 32 formed to be opposed to the first projecting portion 31. The groove portion 40 is formed between the first projecting portion 31 and the second projecting portion 32.

As illustrated in FIG. 4, preferably, the first projecting portion 31 and the second projecting portion 32 are formed into a circular arc shape. As illustrated in FIG. 4, the groove portion 40 is curved so as to bulge toward a CLA direction.

The groove width W of the groove portion 40 is constant along a length direction of the first projecting portion 31 and the second projecting portion 32. In this way, the first projecting portion 31 and the second projecting portion 32 are formed into a circular arc shape, and the groove width W of the groove portion 40 is constant anywhere.

Figure 6:
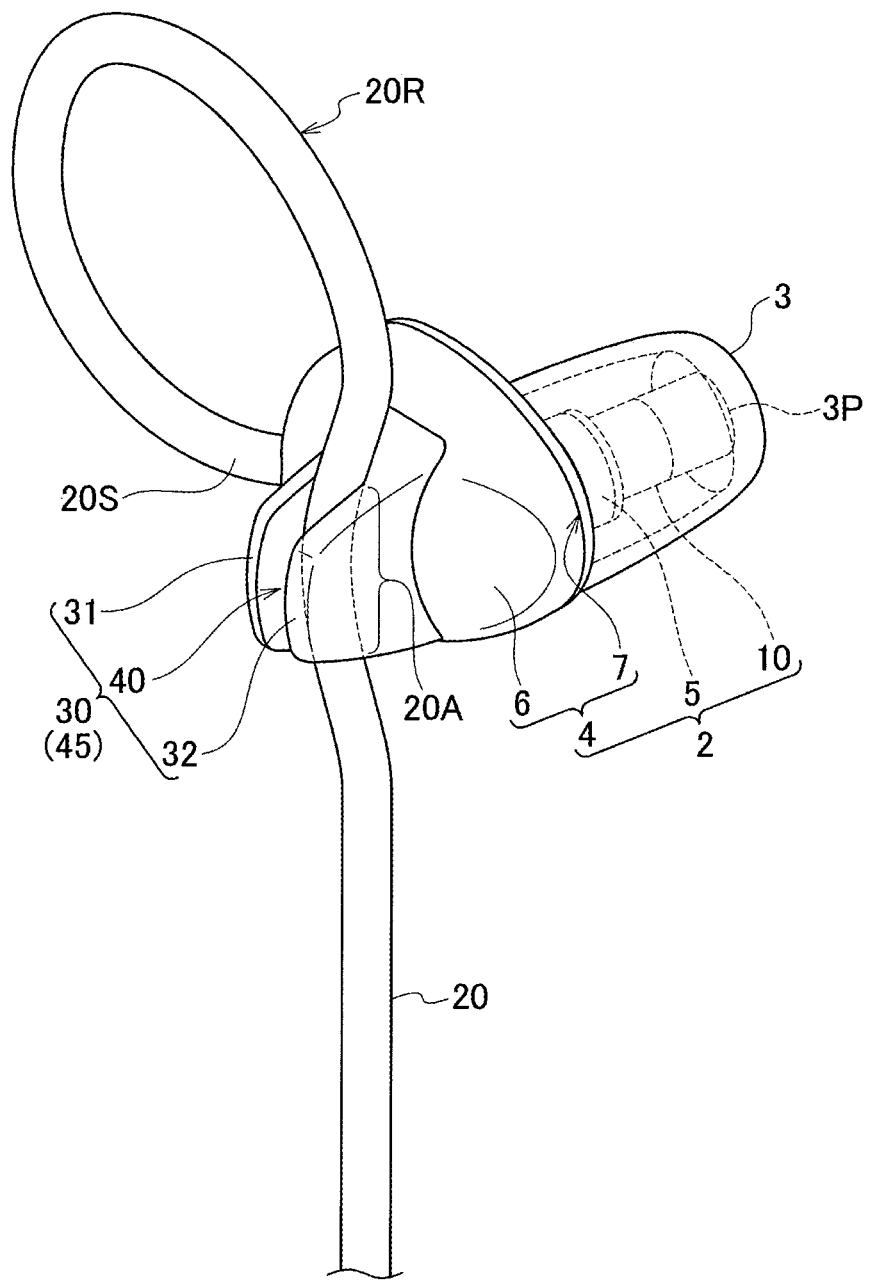
FIG. 6 is a perspective view illustrating a state where, in the thermometer according to the first embodiment, a signal cable is held under condition of being curved in a loop manner

As illustrated in FIGS. 2 and 6, the portion 20A of the signal cable 20 is interposed and held by the groove portion 40. Thus, a portion of the signal cable 20 can be formed into a looped curved part 20R. The curved part 20R can be accommodated in the cavum conchae 109 of the ear 100 so as to be laid along the shape of the cavum conchae 109.

As illustrated in FIGS. 3 and 4, the cable holding part 30 including the first projecting portion 31 and the second projecting portion 32 also functions as a gripping part 45 as a "knob" to be held by fingers of an operator, for example, a thumb F1 and an index finger F2. That is, the function of the cable holding part 30 also serves as the function of the gripping part 45.

Consequently, the operator can pinch and hold respective outer surfaces of the first projecting portion 31 and the second projecting portion 32 by the thumb F1 and the index finger F2.

By pinching and holding the outer surfaces of the first projecting portion 31 and the second projecting portion 32 by the thumb F1 and the index finger F2, the operator can easily and surely insert and fit the probe 2 into the ear canal 104. When the probe 2 is fitted into the ear canal 104 in this way, the infrared sensor 10 is positioned so as to face the eardrum 105 while being separated from the eardrum 105.

Next, the usage example of the thermometer 1 according to the first embodiment will be described.

The ear temperature detection device 300 including the thermometer 1, the controller 200, and the monitor 250 is placed in an operation room, an intensive care unit, or the like in order to continuously and non-invasively measure the body temperature of child patient in a non-contact manner at the time of the surgery in the operation room, the physical condition management in the intensive care unit, or the like.

For example, as illustrated in FIG. 6, the operator preliminarily bends the signal cable 20 in a loop shape, as indicated with the curved part 20R of the signal cable 20, while allowing the portion 20A of the signal cable 20 to be pinched so as to be laid along the groove portion 40 between the first projecting portion 31 and the second projecting portion 32.

Using the cable holding part 30 of the probe 2 as the gripping part 45, the operator holds the first projecting portion 31 and the second projecting portion 32 of the gripping part 45 by the fingers of the operator, for example, the thumb F1 and the index finger F2, as illustrated in FIG. 3. Then, the operator puts the main body part 4 of the probe 2 inside the tragus 108 so that the ear pad 3 is inserted into the ear canal 104.

In this way, the operator can fit the main body part 4 of the probe 2 in the tragus 108 in a state of holding the grip part 45 and also easily and surely perform this fitting operation. When the main body part 4 is accommodated and fitted in the tragus 108, the infrared sensor 10 is arranged so as to face the eardrum 105 at an interval.

At this time, slightly sliding of the signal cable 20 along the groove portion 40 in the G direction by the operator, the size of the curved part 20R of the signal cable 20 can be adjusted according to the size of the cavum conchae 109, as illustrated in FIG. 2. As a result, the curved part 20R of the signal cable 20 can be accommodated and retained in the cavum conchae 109.

As illustrated in FIG. 4, the groove portion 40 is curved so as to bulge in the CLA direction. Accordingly, the groove portion 40 bends and holds the portion 20A of the signal cable 20, while the portion 20A of the signal cable 20 is forcibly bent into a slightly-arc shape by the groove portion 40. Thus, the portion 20A of the signal cable 20 is not easily detached from the groove portion 40.

As illustrated in FIG. 6, by the effect of the groove portion 40 bent into a circular arc shape, it is possible to form the curved part 20R in a substantially circular shape by applying a force to another portion 20S of the signal cable 20 and the portion 20A. Therefore, the curved part 20R of the signal cable 20 can be matched with the shape of the cavum conchae 109.

In this way, the curved part 20R of the signal cable 20 can be accommodated in the cavum conchae 109 of the ear 100 so as to extend along the shape and size of the cavum conchae 109 of an individual child patient.

As a result, it is eliminated that the thermometer 1 is detached or displaced from the ear canal 104. The infrared sensor 10 of the thermometer 1 is capable of stably detecting the amount of infrared rays from the eardrum 105 and its surrounding tissues over a long period of time, at the time of surgery in an operation room, physical condition management in an intensive care unit, or the like.

Besides, as illustrated in FIGS. 1 and 2, the operator can adjust the position of the probe 2 by holding the gripping part 45 in order that the main body part 4 of the probe 2 enters the underside (inside) of the tragus 108 so that the curved part 20R of the signal cable 20 can be correctly fitted to the cavum conchae 109.

The ordinary ear thermometer for adults is different, in the shape of the probe, from each other for the left and right ears. The reason why the shapes of the probe are different from each other for the left and right ears in this way is that the correct temperature has to be acquired by attaching the probe so that the infrared sensor at the tip of the probe faces the eardrum. For this purpose, as the probe of the ear thermometer for adults, it is necessary to prepare two kinds of probes having different shapes which can correspond to two different curved shapes in the ear canal for the left and right ears. That is, since the shapes of the probe become symmetrical like a mirror for the left and right ears, the shapes of the probe have to be different from each other for the left and right ears.

The thermometer for adults is provided with an axis which allows the direction of the probe to be limited when fitting the thermometer into the ear canal. Then, if the thermometer is fitted into the ear canal so that this axis passes between a "tragus" and an "auricle", this means that the probe of the thermometer has been fitted in the correct position. Thus, the thermometer with such an axis has a structure that makes it possible for the operator to visually confirm that the thermometer has been fitted in the correct position.

On the other hand, when the patient is a child (for example, 4 to 12 years old), the degree of bending of the ear hole is small unlike the case that the patient is an adult because the ear hole of the child is smaller than that of the adult. Therefore, the main body part 4 of the probe 2 for children does not include an axis serving as a guide for fitting it into the underside (inside) of the tragus 108 in FIG. 2.

For this reason, for the probe 2 of the thermometer 1 for children, it is necessary to visually exhibit whether or not the probe 2 has been fitted in the correct position, enable the signal cable 20 drawn out of the probe 2 to be routed about the ear 100 appropriately, and allow the thermometer 1 to be retained in the ear 100 stably.

The degree of bending of the ear hole of child is small in comparison with the degree of bending of the ear hole of adult and therefore, the probe 2 of the thermometer 1 according to the first embodiment is smaller than the probe for adults. Assuming that the ear canals of the left and right ears of child are of an identical bending shape, if the probe 2 of the thermometer 1 could cope with such an identical bending shape, the infrared sensor 10 of the probe 2 could be sufficiently oriented in the direction of the eardrum 105. For this reason, the shape of the probe 2 does not require it to be distinguished with respect to each of the left and right ears. Instead, for the probe 2 of the thermometer 1, a necessary probe is only a probe having an identical shape in common.

However, when communalizing the shape of the probe 2 of the thermometer 1 for children in the left and right ears, it becomes not so easy to provide the thermometer with an axis by which the direction of fitting the probe 2 of the thermometer 1 for children into the ear canal 104 can be clarified. The thermometer 1 is preferably a single-use disposable item.

In such a situation, it is considered whether or not the probe 2 of the thermometer 1 could be easily and surely fitted into the ear canal 104 while visually confirming it even if the thermometer 1 has a simpler shape. As a result, the cable holding part 30, which is to be pinched and held by fingers of operator such as a thumb F1 and a index finger F2 and which includes the first projecting portion 31 and the second projecting portion 32, is made to function as the gripping part 45 as a "knob" for fitting the probe 2 into the ear canal 104, as described above and also illustrated in FIG. 3.

Meanwhile, as for the shape of the probe of a thermometer for children, it is also contemplated to fabricate an axis falling down to the left and right corresponding to the structures of the left and right ears. However, it is feared that a structural overstain is produced since the volume of the probe of the thermometer for children is small and that the manufacturing method becomes complicated to cause a cost increase. For these reasons, as for the shape of the probe, we do not adopt a measure of fabricating such an axis falling down to the left and right.

Therefore, in order to allow the main body part 4 of the probe 2 to enter under the tragus 108 so that the thermometer 1 can be stably and correctly fitted into the cavum conchae 109 with no movement, with pinching of the gripping part 45 between the fingers of operator, the operator can easily and surely fit the probe 2 of the thermometer 1 to its correct fitting position while confirming it visually, in spite of no axis serving as a guide during the fitting operation.

In order to make it possible for the operator to visually confirm whether or not the probe 2 has been fitted in the correct position, specifically, the fact that the curved part 20R of the signal cable 20 passes through the inside of "cavum conchae 109" between the "tragus 108" and the "auricle 106" has almost the same meaning as the probe 2 being positioned in its correct fitting position, as illustrated in FIG. 2. Moreover, as illustrated in FIG. 2, when fitting the probe 2, the gripping part 45 allows the signal cable 20 to be slightly inclined at an angle θ to the front side of the patient's face so as to face the direction between the "tragus 108" and "auricle 106", as illustrated with a broken line region RR.

In this way, the groove portion 40 of the gripping part 45 also serving as the cable holding part 30 is formed into a circular arc shape to fit the thermometer 1 to the correct position corresponding to the left and right ears 100. Once the portion 20A of the signal cable 20 is fitted and held in the groove portion 40 of the cable holding part 30, the signal cable 20 does not come off the cable holding part 30. Therefore, the probe 2 can be fitted to the ear of child over a long period of time stably.

Thus, it is possible to exhibit whether or not the probe 2 of the thermometer 1 has been fitted in the correct position, to the operator visually.

In addition, when deviation is caused at the position of the probe 2 during the fitting operation, the value of the obtained body temperature may change or a variation may be caused in the value of the body temperature. Therefore, the thermometer 1 is necessary to prevent the signal cable 20 from coming out of the cable holding part 30 and enable the probe 2 to be stably fitted over a long period of time.

As the coming-off prevention countermeasures for preventing the signal cable 20 from being pulled with a strong force, the operator has only to paste a medical tape TP to a face of patient, thereby affixing and holding a middle portion of the signal cable 20 on the face, as illustrated in FIG. 2. Consequently, even if a strong force is applied to the signal cable 20, the signal cable 20 would not come off the cable holding part 30 and additionally, it is possible to prevent the probe 2 from coming off the ear 100.

On the other hand, in order to prevent the probe 2 from being displaced or dislocated in the ear 100 due to a small movement of the patient, a change in the posture of the patient, or the like, the looped curved part 20R of the signal cable 20 is accommodated in and along the cavum conchae 109 so as to match with the size and shape of the cavum conchae 109. Moreover, the portion 20A of the signal cable 20 is pinched in the groove portion 40 between the first projecting portion 31 and the second projecting portion 32. Consequently, even if there arises a small movement of the patient or a change in the posture of the patient, it is possible to prevent the probe 2 from being displaced or dislocated, so that the thermometer 1 can be stably retained in the ear 100.

In this way, the signal cable 20 drawn out of the probe 2 can be routed about the ear 100 appropriately and additionally, it is possible to retain the thermometer 1 in the ear 100 stably.

Although the thermometer 1 according to the first embodiment is adapted so as to pinch and hold the portion 20A of the signal cable 20 in the groove portion 40 between the first projecting portion 31 and the second projecting portion 32, the position of pinching and fixing the signal cable 20 can be slidably adjusted along the longitudinal direction G of the signal cable 20 arbitrarily. Therefore, the operator can adjust the size of the loop-shaped curved part 20R of the signal cable 20 in accordance with the size of the cavum conchae 109 of the patient.

Next, thermometers according to the other embodiments will be described. In the thermometers according to the other embodiments, elements similar to those of the thermometer 1 according to the first embodiment are indicated with the same reference numerals respectively, and their explanations are omitted.

Second Embodiment

Figure 7:
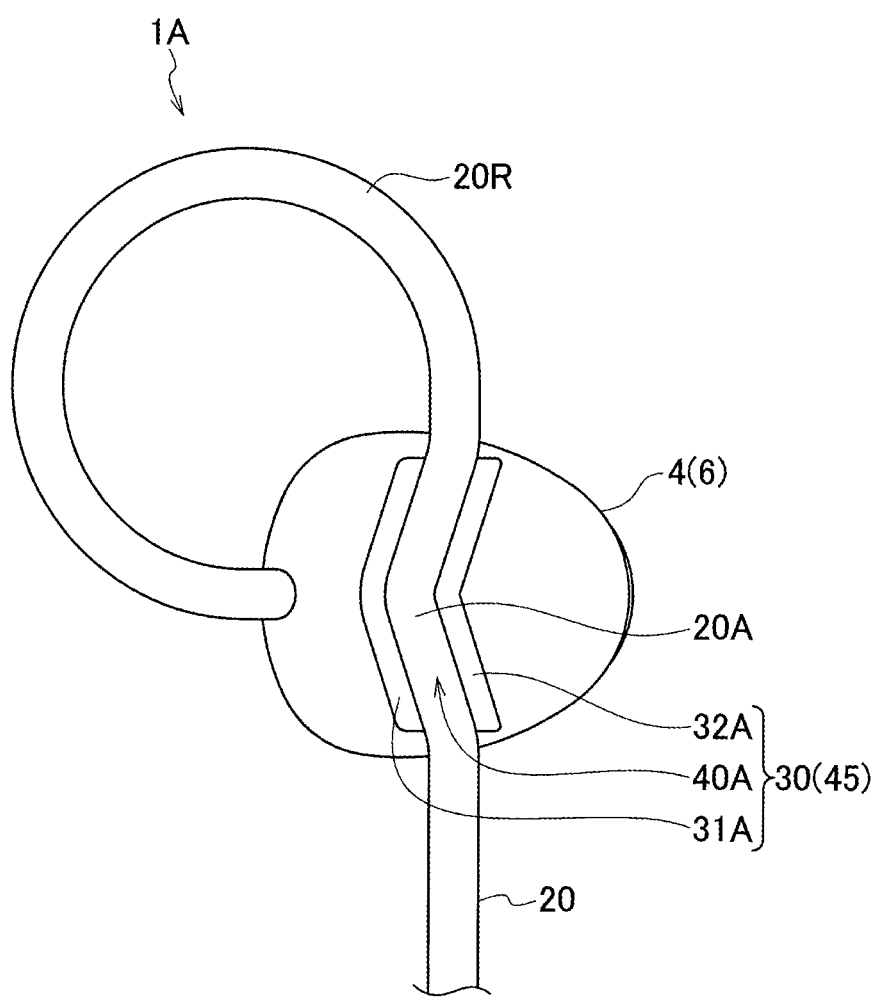
FIG. 7 is a view illustrating a thermometer according to a second embodiment.

FIG. 7 illustrates a thermometer 1A according to a second embodiment.

In the thermometer 1 according to the first embodiment, the groove portion 40 of the cable holding part 30 also serving as the gripping part 45 is formed into a circular arc shape.

On the contrary, in the thermometer 1A according to the second embodiment, the cable holding part 30 also serving as the gripping part 45 includes a first projecting portion 31A and a second projecting portion 32A each formed into a V shape. Therefore, a groove portion 40A between the first projecting portion 31A and the second projecting portion 32A is also formed into a V shape.

Thus, with the thermometer 1A according to the second embodiment, similarly to the thermometer 1 according to the first embodiment, it is possible to accommodate the signal cable 20 in and along the cavum conchae 109 of the ear 100 since the portion 20A of the signal cable 20 is pinched and held in the groove portion 40A.

Third Embodiment

Figure 8:
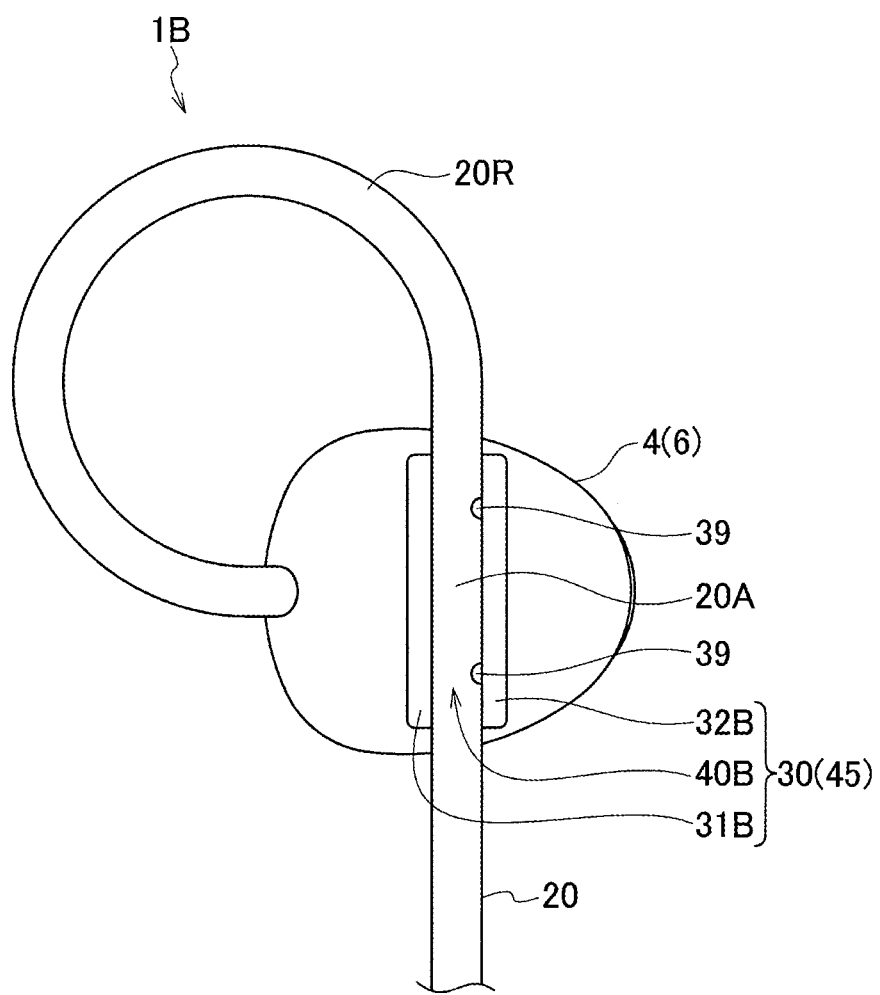
FIG. 8 is a view illustrating a thermometer according to a third embodiment.

FIG. 8 illustrates a thermometer 1B according to a third embodiment.

In the thermometer 1B according to the third embodiment, the cable holding part 30 also serving as the gripping part 45 includes a first projecting portion 31B and a second projecting portion 32B formed into a linear shape. Therefore, a groove portion 40B between the first projecting portion 31B and the second projecting portion 32B is linear. However, the second projecting portion 32B is provided with protrusions 39 inside.

Thus, with the thermometer 1B according to the third embodiment, similarly to the thermometer 1 according to the first embodiment, it is possible to accommodate the signal cable 20 in and along the cavum conchae 109 of the ear 100 since the portion 20A of the signal cable 20 is pinched in the groove portion 40A and further pressed in beyond the protrusions 39.

The thermometer 1, 1A, 1B according to each embodiment includes the probe 2 to be fitted into the ear hole, the probe having the infrared sensor 10 for measuring the temperature of the eardrum 105 of the ear 100 of patient in a non-contact manner, the signal cable 20 connected to the infrared sensor 10 and drawn out of the probe 2, the gripping part 45 provided in the probe 2 to be gripped when the probe 2 is inserted inside the tragus 108 of the ear 100 and the groove portion 40, 40A, 40B provided in the gripping part 45 to hold the signal cable 20 in a curved state and to allow the curved part 20R of the signal cable 20 to fit in and along the cavum conchae 109 of the ear 100.

As a result, the operator can fit the probe 2 into the ear hole with the use of the gripping part 45. Moreover, since the signal cable 20 is held by the groove portion 40, 40A, 40B of the gripping part 45, it is possible to allow the curved part 20R of the signal cable 20 to fit in and along the cavum conchae 109 of the ear 100 and also possible to retain the probe 2 in the ear 100 together with the signal cable 20.

Therefore, the thermometer 1 can be easily and reliably fitted into the ear hole of the ear 100 of child and can continuously measure the body temperature in a stable state where the thermometer 1 does not come off the ear hole.

The grip part 45 includes the groove portion 40, 40A, 40B for pinching and holding the portion 20A of the signal cable 20. Thus, by only pinching and retaining the signal cable 20 in the groove portion 40, 40A, 40B, it is possible to allow the signal cable 20 in a curved state to easily and reliably fit in and along the cavum conchae 109 of the ear.

The gripping part 45 includes the first projecting portion 31, 31A, 31B and the second projecting portion 32, 32A, 32B formed to face the first projecting portion 31, 31A, 31B, and the groove portion 40, 40A, 40B is formed between the first projecting portion 31, 31A, 31B and the second projecting portion 32, 32A, 32B. Thus, the groove portion 40, 40A, 40B is only defined by the first projecting portion 31, 31A, 31B and the second projecting portion 32, 32A, 32B. While having a simple structure, the first projecting portion 31, 31A, 31B and the second projecting portion 32, 32A, 32B hold the signal cable 20 and moreover, the operator can grip the first projecting portion 31, 31A, 31B and the second projecting portion 32, 32A 32B with fingers.

The groove portion 40, 40A bends the portion 20A of the signal cable 20 into a circular arc shape or a V shape and holds the same portion. Thus, by only forming the groove portion 40, 40A into a circular arc shape or a V shape, the first projecting portion 31, 31A and the second projecting portion 32, 32A hold the signal cable 20 with a simple structure and moreover, the operator can grip the first projecting portion 31, 31A, 31B and the second projecting portion 32, 32A 32B with fingers.

Although the present application has been described with reference to the embodiments, each embodiment is nothing but one example and therefore, the scope of the application described in the claims may be variously changed within the scope not deviating from the gist of the application, and the respective embodiments of the present application may be combined arbitrarily.

For example, the shape of the probe 2 is not limited to the illustrated example and may be replaced with the other shape.

In the gripping part 45 (the cable holding portion 30), the first projecting portion 31, 31A, 31B and the second projecting portion 32, 32A, 32B may be formed, on their respective outer surfaces, with nonslip irregularities for providing a nonslip property when being handled by the fingers.

What is claimed is:

1. A thermometer, comprising:
a probe to be fitted into an ear hole of a patient, the probe having an infrared sensor for measuring the temperature of an eardrum of an ear of the patient in a non-contact manner;
a signal cable connected to the infrared sensor and drawn out of the probe;
a gripping part provided in the probe to be gripped when the probe is inserted inside a tragus of the ear; and
a groove portion provided in the gripping part and configured so as to pinch and hold a portion of the signal cable, the groove portion pinching and holding the portion of the signal cable in a state where the signal cable is curved, and a curved portion of the signal cable accommodated in a cavum conchae of the ear so as to be laid the curved portion along the cavum conchae when the probe is fitted into the ear hole.

2. The thermometer of claim 1, wherein
the gripping part includes a first projecting portion and a second projecting portion formed to face the first projecting portion, and
the groove portion is formed between the first projecting portion and the second projecting portion.

3. The thermometer of claim 1, wherein
the groove portion is configured so as to bend a portion of the signal cable into a circular arc shape or a V shape and hold the portion of the signal cable.

* * * * *